United States Patent [19]

Schmiechen et al.

[11] Patent Number: 4,945,090
[45] Date of Patent: Jul. 31, 1990

[54] PHENOXY-SUBSTITUTED BETA-CARBOLINE DERIVATIVES, THEIR PRODUCTION AND THEIR USE AS DRUGS

[75] Inventors: Ralph Schmiechen; Dieter Seidelmann; Andreas Huth; Herbert H. Schneider; David N. Stephens, all of Berlin, Fed. Rep. of Germany; Mogens Engelstoft, Vaerlose, Denmark; John B. Hansen, Lyngby, Denmark; Erling Petersen, Glostrup, Denmark

[73] Assignee: Schering Aktiengesellschaft, Berlin and Bergkamen, Fed. Rep. of Germany

[21] Appl. No.: 929,861

[22] Filed: Nov. 13, 1986

[30] Foreign Application Priority Data

Nov. 13, 1985 [DE] Fed. Rep. of Germany ....... 3540654

[51] Int. Cl.⁵ .................. A61K 31/38; A61K 31/435; C07D 471/04
[52] U.S. Cl. .................... 514/232.8; 544/60; 544/126; 544/361; 546/86; 514/228.2; 514/253; 514/292
[58] Field of Search ............... 546/86; 514/292, 228.2, 514/232.8, 253; 544/60, 126, 361

[56] References Cited

FOREIGN PATENT DOCUMENTS 0130140 6/1984 European Pat. Off. ............ 514/292

*Primary Examiner*—Mary C. Lee
*Assistant Examiner*—J. Richter
*Attorney, Agent, or Firm*—Millen, White & Zelano

[57] ABSTRACT

Phenoxy-substituted beta-carbolines of the formula I

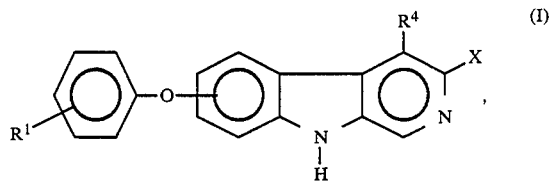

$X$ is $COOR^3$, $CONHC_{1-3}$-alkyl or oxadiazolyl of the formula

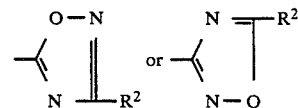

$R^2$ is H, lower alkyl or cycloalkyl,
$R^3$ is lower alkyl,
$R^4$ is hydrogen, lower alkyl or lower alkoxyalkyl,
$R^1$ is hydrogen, halogen, lower alkyl, lower alkoxy, acyl, phenyl, $C_{2-5}$ alkylenedioxy, trifluoromethyl, nitrilo, nitro, lower alkoxycarbonyl, azido, $SO_2R^6$, $SO_2NR^7R^8$, or $NR^9R^{10}$,
$R^6$ is lower alkyl,
$R^7$ and $R^8$ independently are lower alkyl or together with the nitrogen atom form a hetero ring,
$R^9$ and $R^{10}$ independently are hydrogen, lower alkyl, acyl or together with the nitrogen atom form a hetero ring system, with the proviso that X is not COOEt, if

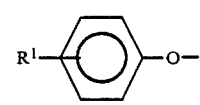

is 5-phenoxy and $R^4$ is methyl or

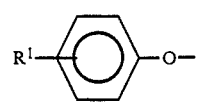

is 6-(4-methoxyphenoxy) and $R^4$ is methoxymethyl have valuable pharmacological properties.

22 Claims, No Drawings

PHENOXY-SUBSTITUTED BETA-CARBOLINE DERIVATIVES, THEIR PRODUCTION AND THEIR USE AS DRUGS

BACKGROUND OF THE INVENTION

This invention relates to new phenoxy-substituted beta-carboline derivatives, their production and their use as drugs.

In EP-A-130140, which discloses the 6-(4-methoxyphenoxy)-4-methoxymethyl-beta-carboline-3-carboxylic acid ethyl ester, and in EP-A-54507, which discloses the 5-phenoxy-4-methyl-beta-carboline-3-carboxylic acid ethyl ester, compounds are described which have the known action of beta-carbolines on the central nervous system.

SUMMARY OF THE INVENTION

It is an object of this invention to provide new beta-carbolines having valuable pharmacological properties.

Upon further study of the specification and appended claims, further objects and advantages to this invention will become apparent to those skilled in the art.

These objects have been attained by providing the compounds according to the invention of the formula I

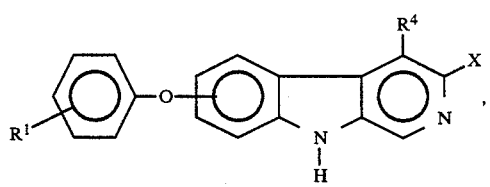

wherein

X is $COOR^3$, $CONHC_{1-3}$-alkyl or oxadiazolyl of the formula

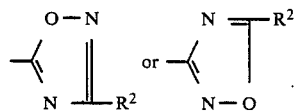

$R^2$ is H, lower alkyl or cycloakyl,
$R^3$ is lower alkyl,
$R^4$ is hydrogen, lower alkyl or lower alkoxyalkyl,
$R^1$ is hydrogen, halogen, lower alkyl, lower alkoxy, acyl, phenyl, $C_{2-5}$ alkylenedioxy, trifluoromethyl, nitrilo, nitro, lower alkoxycarbonyl, azido, $SO_2R^6$, $SO_2NR^7R^8$, $NR^9R^{10}$,
R6 is lower alkyl,
$R^7$ and $R^8$ independently are lower alkyl or together with the nitrogen atom form a hetero ring or
$R^9$ and $R^{10}$ independently are hydrogen, lower alkyl, acyl or together with the nitrogen atom form a hetero ring system,
with the proviso that X is not COOEt, if

is 5-phenoxy and $R^4$ is methyl or

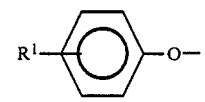

is 6-(4-methoxyphenoxy) and $R^4$ is methoxymethyl.

The new beta-carboline derivatives of formula I can be substituted once or twice in the A ring in positions 5-8. Substitution in the 5 or 6 position is preferred.

Substituent $R^1$ can occur one or more (up to 5) time, preferably 1-3 times on the aryl radical. The $R^1$ groups can be the same or different. Suitable lower alkyl groups and alkyl portions throughout include both straight-chain and branched-chain radicals of 1-6 carbon atoms. For example, there can be mentioned the preferred $C_{1-4}$ alkyl radicals such as methyl, ethyl, n-propyl, isopropyl, n-butyl, isobutyl, tert-butyl and sec-butyl. Also suitable are heptyl and hexyl groups.

Suitable cycloalkyl groups $R^2$ include those of 3-7 carbon atoms, preferably of 3-5 carbon atoms, for example, cyclopropyl, methyl cyclopropyl, cyclobutyl, cyclopentyl, etc. Also suitable are cyclohexyl and cycloheptyl.

The acyl radical is preferably derived from aliphatic carboxylic acids of up to 4 carbon atoms, e.g., alkanoyl, formic acid, acetic acid, propionic acid, butyric acid, etc.

If $R^7R^8$ and $R^9R^{10}$ together with the nitrogen atom form a heterocycle, then the latter is 5-6 membered and saturated, and one or two $CH_2$ groups can be replaced by oxygen, sulfur or nitrogen. For example, the following non-limiting examples can be mentioned: imidazolidinyl, pyrazolidinyl, piperidinyl, pyrrolidinyl, piperazinyl, morpholinyl, thiomorpholinyl, isothiazolidinyl, etc.

Suitable halogens include fluorine, chlorine, bromine and iodine.

The compounds according to the invention surprisingly show superior psychotropic properties in pharmacological tests in comparison with previously known beta-carbolines as can be seen from the table by the example of some compounds according to the invention.

The compounds according to the invention especially show anxiolytic and anticonvulsive effectiveness. For demonstration of the anticonvulsive action, stopping of spasms induced by pentylenetrazole (pentazol) was examined. Pentazol is administered subcutaneously in an amount of 150 mg/kg as hydrochloric acid solution (pH 2-3) 15-30 minutes after the intraperitoneal application of the test substance. This amount induces clonic and tonic spasms, which lead to death in untreated animals. The number of mice which show spasms and the number of them that died 30 minutes after pentazol are recorded (PTZ spasms antagonism).

The $ED_{50}$ values indicated in the table were determined according to the method of Litchfield and Wilcoxon (J. Pharmacol. exp. Ther. 96 (1949) 99-103) as the amount of antagonistically acting substance which protects 50% of the animals from spasms and death.

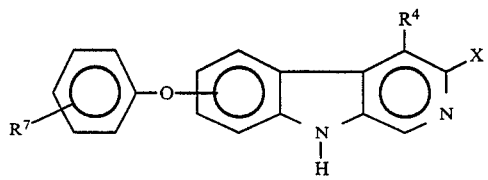

| R1 | R4 | X | IC$_{50}$ (ng/ml) in vitro | ED$_{50}$ (mg/kg) in vivo | PTZ (ED$_{50}$) mg/kg in vivo |
|---|---|---|---|---|---|
| 5-Phenoxy | CH$_3$ | COOC$_2$H$_5$ | 2.0 | 2.8 | >30 |
| 5-(2-Cl-Phenoxy) | CH$_2$OCH$_3$ | O—N, N, Et (oxadiazole-Et) | 3.1 | 11 | 0.8 |
| 5-(2-Cl-Phenoxy) | CH$_2$OCH$_3$ | —COOCH(CH$_3$)$_2$ | 2.6 | 19 | 4 |
| 5-(2-4-dichlorphenoxy) | CH$_2$OCH$_3$ | —COOC$_2$H$_5$ | 2.9 | 3.2 | 4 |
| 6-(2-nitrophenoxy) | CH$_2$OCH$_3$ | —COOCH(CH$_3$)$_2$ | 0.33 | 1.8 | 13 |
| 6-(2-cyano-3-Cl-Phenoxy) | CH$_2$OCH$_3$ | —COOCH(CH$_3$)$_2$ | 0.67 | 3.0 | 1 |
| 6-(2-cyanophenoxy) | CH$_2$OCH$_3$ | —COOCH(CH$_3$)$_2$ | 0.29 | 3.8 | 4 |
| 6-(4-acetylphenoxy) | CH$_2$OCH$_3$ | O—N, N, Et | 0.45 | 7.7 | 0.3 |
| 5-Phenoxy | CH$_2$OCH$_3$ | —COOEt | 0.3 | 0.4 | 18 |
| 5-Phenoxy | CH$_2$OCH$_3$ | O—N, N, Et | 0.6 | 0.3 | 0.1 |
| 5-Phenoxy | CH$_3$ | O—N, N, Et | 4.3 | 3.9 | 2 |
| 6-Phenoxy | CH$_3$ | O—N, N, Et | 3.2 | 2.6 | 2.4 |

It is known that certain sites in the central nervous system of vertebrates exhibit a great specific affinity for the binding of 1,4- and 1,5-benzodiazepines (Squires, R. F. and Braestrup, C., Nature (London) 266 (1977) 734). The binding sites are called benzodiazepine receptors. The pharmacological properties of the compounds according to the invention were determined by examination of their capability to displace radioactively marked flunitrazepam from benzodiazepine receptors. The displacement activity of the compounds according to the invention is indicated as IC$_{50}$ and ED$_{50}$ values.

The IC$_{50}$ value indicates the concentration, which causes a 50% displacement of the specific binding of H$^3$-flunitrazepam (1.0 nM, 0° C.) in samples with a total volume of 0.55 ml of a suspension of brain membranes, e.g., of rats. The displacement test is performed as follows:

0.5 ml of a suspension of untreated rat forebrain in 25 mM KH$_2$PO$_4$, pH=7.1 (5–10 mg of tissue/sample) is incubated for 40–60 minutes at 0° C. together with $^3$H-diazepam (specific activity 14.4 Ci/mmol, 1.9 nM) or $^3$H-flunitrazepam (specific activity 87 Ci/mmol, 1.0 nM). After incubation, the suspension is filtered through a glass filter, the residue is washed twice with cold buffer solution and the radioactivity is measured on the scintillation counter. The test was then repeated but so that before addition of the radioactively marked benzodiazepine a specific amount or an excess amount of the compound, whose displacement activity is to be determined, is added. The IC$_{50}$ value can be calculated on the basis of the values obtained.

The ED$_{50}$ value represents the dose of a test substance, which causes a reduction of the specific binding of the flunitrazepam on the benzodiazepine receptor in a live brain to 50% of the control value. The in vivo test is performed as follows:

The test substance is injected into groups of mice in different doses and normally intraperitoneally. After 15 minutes the $^3$H-flunitrazepam is administered intravenously to the mice. After another 20 minutes the mice are sacrificed, their forebrain is removed and the radioactivity specifically linked to the brain membrane is measured by scintillation counting. The ED$_{50}$ value is determined from the dose/action curves.

The new compounds of general formula I have valuable pharamcological properties. They particularly affect the central nervous system and thus are suitable as psychotropic drugs for human medicine, whereby they are used especially for treatment of anxiety accompanied by depressions, epilepsy, sleep disturbances, spasticities and muscle relaxation during anesthesia. The also display amnestic or memory-promoting properties.

The compounds according to the invention can be used for formulation of pharmaceutical preparations, for example, for oral and parenteral application to mammals, including humans, according to galenic methods known in the art.

Suitable inactive ingredients for formulation of pharamceutical preparations are those physiologically compatible organic and inorganic vehicles for enteral and parenteral application, which are inert in regard to the compounds according to the invention. As vehicles can be named, for example, water, salt solutions, alcohols, polyethylene glycols, polyhydroxyethoxylated castor oil, gelatins, lactose, amylose, magnesium stearate, talc, silicic acid, fatty acid mono and diglycerides, pentaerythritol fatty acid ester, hydroxymethylcellulose and polyvinylpyrrolidone.

The pharmaceutical preparations can be sterilized and/or mixed with inactive ingredients such as lubricants, preservatives, stabilizers, wetting agents, emulsifiers, buffering agents and dyes.

For parenteral application especially suitable are injection solutions or suspensions, especially aqueous solutions of the active compounds in polyhydroxyethyoxylated castor oil.

For oral application are suitable especially tablets, sugar-coated tablets or capsules with talc and/or a hydrocarbon vehicle or binding agent, such as, for example lactose, corn or potato starch. Administration can take place also in liquid form, for example, as a juice to which optionally a sweetening agent is added.

The compounds according to the invention are utilized generally in a dose unit of 0.05 to 100 mg of active substance in a physiologically compatible vehicle. The compounds according to the invention are administered in a dose of 0.1 to 300 mg/day, preferably 1-30 mg/day, as anxiolytics or anticonvulsants analogously to, e.g., the known agent, diazepam.

Production of the compounds of formula I according to the invention takes place according to known methods.

For example, production of the compounds of general formula I can be conducted by (a) reacting a compond of formula II

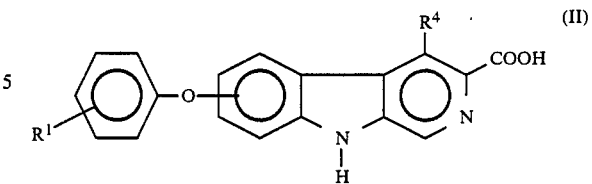

wherein R$^1$ and R$^4$ have the above-mentioned meanings, with a compound of the formula

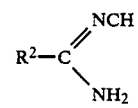

wherein R$^2$ has the above-mentioned meanings, to form a compound of formula, I, in which X stands for the radical

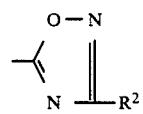

where R$^2$ has the above-mentioned meaning,
or esterifying or amidating a compound of formula II, (b) reacting a compound of formula III

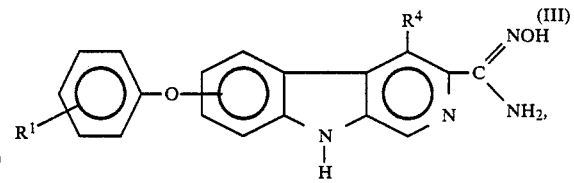

wherein R$^1$ and R$^4$ have the above-mentioned meanings,
with a carboxylic acid anhydride (R$^2$CO)$_2$O, wherein R$^2$ has the above-mentioned meanings,
to form a compound of formula I, in which X stands for the radical

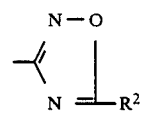

with R$^2$ having the above-mentioned meanings, (c) reacting a compound of formula IV

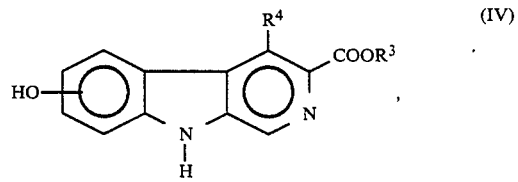

wherein R$^3$ and R$^4$ have the above-mentioned meanings,
with a compound of the formula

wherein $R^1$ has the above indicated meanings and $R^{1'}$ represents an electrophilic substituent, and then, optionally, (α) reducing a nitro group to an amino group and, if desired, deaminating the amino group thus obtained or exchanging it for halogen or azide, or (β) if $R^1$ is halogen, catalytically dehalogenating it, or (γ) transesterifying or saponifying an ester group and, if desired, amidating the carboxylic acid thus obtained.

Hal is halogen, preferably fluorine or chlorine, in the foregoing.

For the introduction of the 1,2,4-oxadiazol-5-yl radical the beta-carboline carboxylic acid of general formula II along with an amidoxime of the formula

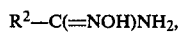

in an inert solvent, which boils above 100° C. and is inert to the reactant, is brought to condensation at the reflux temperature of the reaction mixture. Suitable solvents for the condensation reaction are, for example, toluene and dimethylformamide. Appropriately, the free beta-carboline-3-carboxylic acid is suitably activated before the condensation reaction. For this purpose, the free acid can be converted, for example, into a mixed anhydride, into an activated ester or into the chloride.

Activation to imidazolide has also proved successful with imidazole/thionyl chloride (or also carbonyldiimidazole) in an aprotic solvent such as dioxane, tetrahydrofuran, dimethylformamide or N-methylpyrrolidone at temperatures between 0° and 50° C., preferably room temperature.

For the introduction of the 1,2,4-oxadiazol-3-yl radical, for example, 3-carboxylic acid nitrile can be reacted with hydroxylamine to form a compound of formula III. The beta-carboline-3-carboxamidoxime thus obtained is mixed with the acid anhydride $(R^2CO)_2O$ at room temperature and then heated to boiling temperature. The reaction is ended after about 7 hours and working up is done according to the usual process.

Introduction of the phenoxy radical takes place preferably by reaction of a compound of formula IV with a fluorobenzene derivative, which suitably carries another electrophilic substituent. As electrophilic substituents $R^{1'}$ the following radicals described for $R^1$ can be mentioned: nitro, lower alkoxycarbonyl, lower alkylsulfonyl, trifluoromethyl, cyano, etc.

The reaction with the substituted halobenzene derivative is performed in a basic medium in dipolar aprotic solvents at temperatures up to the boiling point of the solvent. For example, dimethylsulfoxide, dimethylacetamide, n-methylpyrrolidone, hexamethylphosphoramic triamide, etc., are suitable as solvents. Suitable bases include alkali compounds such as, for example, sodium or potassium hydroxide, sodium or potassium carbonate, etc., optionally also in the presence of phase transfer catalysts as, for example, crown ethers such as 18-crown-6, dicyclohexyl-18-crown-6, dibenzo-18-crown-6 or Aliquat 336. Suitably, the operation is performed under an inert gas atmosphere, for example, under nitrogen or argon.

The reduction of the nitro group to the amino group can take place, for example, catalytically in polar solvents at room temperature. Preferably, palladium on a support such as carbon or platinum in finely divided form is used as catalyst; in the case of compounds with halogen, Raney nickel is preferably used as catalyst. All inert solvents are suitable for the reduction, for example, alcohols or ethers such as methanol, ethanol, diethyl ether, tetrahydrofuran or their mixtures, etc. Hydrogenation can be performed under normal pressure or $H_2$ pressure.

Deamination takes places, for example, according to the Sandmeyer process known in the literature. In this case, a diazonium compound produced intermediately with a nitrite in the presence of copper(I) oxide and hypophosphoric acid is boiled down at elevated temperature.

The introduction of halogens chlorine, bromine or iodine by the amino group can, for example, take place according to Sandmeyer by reacting the diazonium salts (formed intermediately with nitrites) with Cu(I) chloride or Cu(I) bromide in the presence of the corresponding acid, hydrochloric acid or hydrobromic acid or with potassium iodide. Introduction of fluorine can be done, for example, by Balz-Schniemann reaction of diazonium tetrafluoroborate. Introduction of the azido group takes place by Sandmeyer reaction of the diazonium salt with alkali azide, for example.

The catalytic dehalogenation is, for example, performed with palladium on carbon (10%) with addition of organic bases, for example, triethylamine, etc., in alcohols. To avoid transesterification, the alcohol of the ester component suitably is used as solvent.

If a transesterification is desired, it is possible to carry out the reaction, for example, with the corresponding alcohol or alkali metal alcoholate. Optionally, titanium tetraisopropylate can be added in water-free alcohol as catalyst. The transesterification usually is performed at temperatures of 60°-120° C. and is ended after about 2-6 hours.

Introduction of the tert-butyl ester group takes place, for example, by reaction of the carboxylic acid with tertbutoxy-bis-dimethyl-aminomethane. The reaction is generally performed under inert gas atmosphere such as argon or nitrogen and with exclusion of moisture at elevated temperature.

Thus, the saponification of the ester group can take place in an acidic or alkaline manner; preferably it is saponified in an alkaline manner, by the ester being heated to temperatures up to the reflux temperature of the reaction mixture with dilute aqueous lye such as potassium or sodium hydroxide in a protic solvent such as, for example, methanol, ethanol or ethylene glycol.

Carboxylic acid amides are obtained, for example, by reaction with amines of the corresponding imidazolides, which are intermediately produced from carboxylic acids and carbonyldiimidazole or thionyldiimidazole. The reaction is performed at room temperature in diploar aprotic solvents, as for example, dimethylformamide, dimethylacetamide, etc.

The production of the initial compounds is known or takes places according to known processes, as described, for example, in EP-A-130140.

Thus, the esters can be produced by activation of the corresponding acid and then reaction with the desired alcohol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLES

EXAMPLE 1

5-(4-chlorophenoxy)-3-(3-ethyl-1,2,4-oxadiazol-5-yl)-4-methoxymethyl-beta-carboline 5.74 g of 5-(4-chlorophenoxy)-4-methoxymethyl-beta-carboline-3-carboxylic acid are dissolved in 150 ml of absolute dimethylformamide, mixed with 2.91 g of carbonyldiimidazole and stirred for 3 hours at room temperature. To this solution is added 3.96 g of propionamidoxime, it is stirred for 8 hours, 1 g of propionamidoxime is added once more and also stirred for 8 hours. After evaporation on the oil pump vacuum, it is taken up in toluene and refluxed for 8 hours. After evaporation, it is chromatographed twice over silica gel, first with methylene chloride/ethanol=10:1 and then with hexane: acetone=1:1 as eluant. After recrystallization from ethyl acetate/hexane and drying over phosphorus pentoxide at 80° C. in a vacuum, 2.2 g of 5-(4-chlorophenoxy-3-(3-ethyl-1,2,4-oxadizaol-5-yl)-4-methoxymethyl-beta-carboline with a melting point of 170° C. is obtained.

Analogously there are produced:

5-phenoxy-4-methyl-3-(3-ethyl-1,2,4-oxadizaol-5-yl)-beta-carboline
melting point 245°-248° C.

5-(4-nitrophenoxy)-3-(3-ethyl-1,2,4-oxadizaol-5-yl)-beta-carboline
melting point 290° C.

5-(4-chlorophenoxy)-4-methyl-3-(3-ethyl-1,2,4-oxadizaol-5-yl)-beta-carboline
melting point 193°-194° C.

6(4-acetylphenoxy)-4-methoxymethyl-3-(3-ethyl-1,2,4-oxadizaol-5-yl)-beta-carboline
melting point 213°-216° C.

5-(4-nitrophenoxy)-4-methyl-3-(3-ethyl-1,2,4-oxadiazol-5-yl)-beta carboline
melting point 287° C.

5-(4-nitrophenoxy)-4-methoxymethyl-3-(3-ethyl-1,2,4-oxadiazol-5-yl)-beta carboline
melting point 125°-180° C.

5-phenoxy-4-methoxymethyl-3-(3-ethyl-1,2,4-oxadiazol-5-yl)-beta carboline
melting point 168°-171° C.

6-phenoxy-3-(3-ethyl-1,2,4-oxadiazol-5-yl)-beta carboline
melting point 205°-208° C.

6-phenoxy-4-methyl-3-(3-ethyl-1,2,4-oxadiazol-5-yl)-beta carboline
melting point 247°-250° C.

6-(4-nitrophenoxy)-3-(3-ethyl-1,2,4-oxadiazol-5-yl)-beta carboline
melting point 288°-294° C.

6-(4-aminophenoxy)-3-(3-ethyl-1,2,4-oxadiazol-5-yl)-beta carboline
melting point 207°-210° C.

6-(4-chlorophenoxy)-4-methyl-3-(3-ethyl-1,2,4-oxadiazol-5-yl)-beta carboline
melting point 245°-250° C.

6-(4-nitrophenoxy)-4-methyl-3-(3-ethyl-1,2,4-oxadiazol-5-yl)-beta carboline
melting point 250°-258° C.

6-(4-aminophenoxy)-4-methyl-3-(3-ethyl-1,2,4-oxadiazol-5-yl)-beta carboline
melting point 245°-255° C.

6-(4-chlorophenoxy)-4-methoxymethyl-3-(3-ethyl-1,2,4-oxadiazol-5-yl)-beta carboline
melting point 178°-192° C.

6-(4-chlorophenoxy)-4-methoxymethyl-3-(3-cyclopropyl-1,2,4-oxadiazol-5-yl)-beta carboline
melting point 192°-193° C.

6-(4-bromophenoxy)-4-methoxymethyl-3-(3-ethyl-1,2,4-oxadiazol-5-yl)-beta carboline
melting point, greater than 280° C.

6-phenoxy-4-methoxymethyl-3-(3-ethyl-1,2,4-oxadiazol-5-yl)-beta carboline
melting point 164° C.

6-(4-nitrophenoxy)-4-methoxymethyl-3-(3-ethyl-1,2,4-oxadiazol-5-yl)-beta carboline
melting point 223°-225° C.

6-(4-nitrophenoxy)-4-methoxymethyl-3-(3-cyclopropyl-1,2,4-oxadiazol-5-yl)-beta carboline
melting point 226° C.

6-(2-nitrophenoxy)-4-methoxymethyl-3-(3-ethyl-1,2,4-oxadiazol-5-yl)-beta carboline
melting point 206°-211° C.

6-(2-nitrophenoxy)-4-methoxymethyl-3-(3-cyclopropyl-1,2,4-oxadiazol-5-yl)-beta carboline
melting point 154°-155° C.

6-(aminophenoxy)-4-methoxymethyl-3-(3-ethyl-1,2,4-oxadiazol-5-yl)-beta carboline
melting point 249°-255° C.

6-(2-methyl-4-nitrophenoxy)-4-methoxymethyl-3-(3-ethyl-1,2,4-oxadiazol-5-yl)-beta carboline
melting point 208°-209° C.

6-(4-morpholinosulfamoylphenoxy)-4-methoxymethyl-3-(3-ethyl-1,2,4-oxadiazol-5-yl)-beta carboline
melting point 113° C.

6-(4-morpholinosulfamoylphenoxy)-4-methoxymethyl-3-(3-cyclopropyl-1,2,4-oxadiazol-5-yl)-beta carboline
melting point 139°-140° C.

6-(4-diethylsulfamoylphenoxy)-4-methoxymethyl-3-(3-ethyl-1,2,4-oxadiazol-5-yl)-beta carboline
melting point 184°-189° C.

6-(4-methylsulfonylphenoxy)-4-methoxymethyl-3-(3-ethyl-1,2,4-oxadiazol-5-yl)-beta carboline
melting point 150° C.

6-(4-ethoxycarbonylphenoxy)-4-methoxymethyl-3-(3-ethyl-1,2,4-oxadiazol-5-yl)-beta carboline
melting point 185°-191° C.

6-(2-chlorophenoxy)-4-methoxymethyl-3-(3-ethyl-1,2,4-oxadiazol-5-yl)-beta carboline
melting point 158°-161° C.

6-(4-cyanophenoxy)-4-methoxymethyl-3-(3-ethyl-1,2,4-oxadiazol-5-yl)-beta carboline
melting point 224°-225° C.

6-(2-chloro-4-nitrophenoxy)-4-methoxymethyl-3-(3-ethyl-1,2,4-oxadiazol-5-yl)-beta carboline
melting point 200°-213° C.

6-(2-chloro-4-aminophenoxy)-4-methoxymethyl-3-(3-ethyl-1,2,4-oxadiazol-5-yl)-beta carboline
melting point 235°-247° C.

6-(2,4-dichlorophenoxy)-4-methoxymethyl-3-(3-ethyl-1,2,4-oxadiazol-5-yl)-beta carboline melting point 160°–174° C.

6(4-fluorophenoxy)-4-methoxymethyl-3-(3-ethyl-1,2,4-oxadiazol-5-yl)-beta carboline
melting point 240°–242° C.

5(3-chlorophenoxy)-4-methoxymethyl-3-(3-ethyl-1,2,4-oxadiazol-5-yl)-beta carboline
melting point 170°–172° C.

EXAMPLE 2

4-Methoxymethyl-5-phenoxy-3-(3-(5-ethyl-1,2,4-oxadiazol)-yl-beta-carboline 0.7 mmol of 4-methoxymethyl-5-phenoxy-beta-carboline-3-carboxamidoxime and 1 ml of propionic acid anhydride are stirred for 2 hours at 20° C. and then for 5 hours at 120° C. After concentration, 10 ml of tetrahydrofuran is added, the reaction mixture is allowed to stand overnight, then concentrated in a vacuum and the reaction product is extracted with 30 ml of methylene chloride as oily substance.

The initial material is produced as follows:

(a)
5-phenoxy-4-methoxymethyl-beta-carboline-3-carboxamide 2.7 g of 5-phenoxy-4-methoxymethyl-beta-carboline-3-carboxylic acid is added to a solution of 30 mmol of thionyldiimidazole in 150 ml of tetrahydrofuran. The reaction mixture is stirred for 5 hours and filtered. The filtrate is mixed with 12 ml of 25% $NH_3$ in water, stirred overnight and concentrated in a vacuum to 50 ml. After addition of 100 ml of water, 2 g of the desired product is obtained as yellow crystals.

(b)
5-phenoxy-3-cyano-4-methoxymethyl-beta-carboline 1.1 g of $Br_2$ in 10 ml of methylene chloride is put in drop by drop into a stirred solution of 1.8 g (15 mmol) of triphenylphosphine in 50 ml of methylene chloride at 0° C. Then, 2 g of 5-phenoxy-4-methoxymethyl-beta-carboline-3-carboxamide and 1.9 ml of triethylamine are added. The reaction mixture is stirred for 1 hour at 0° C. and then vigorously stirred with 25 ml of methylene chloride and 25 ml of water for 5 minutes. After removal of the aqueous phase from the organic phase by concentration, 0.8 g of the desired product is obtained.

(c)
4-methoxymethyl-5-phenoxy-beta-carboline-3-carboxamidoxime

A mixture of 329 mg (0.001 mol) of 3-cyano-4-methoxymethyl-5-phenoxy-beta-carboline, 100 mg of hydroxylamine hydrochloride, 20 ml of ethanol (99%) and 0.52 ml of a 20% aqueous potassium carbonate solution is refluxed for 22 hours. The reaction mixture is filtered and the filtrate concentrated. The residue is mixed with 10 ml of water, the crystalline solid is filtered off and washed with water.

EXAMPLE 3

5-(4-nitrophenoxy)-4-methoxymethyl-beta-carboline-3-carboxylic acid ethyl ester 6 g of 5-hydroxy-4-methoxymethyl-beta-carboline-3-carboxylic acid ethyl ester under nitrogen in 200 ml of dimethylformamide is mixed with 5.5 g of water-free potassium carbonate and stirred for 1 hour at room temperature.

After mixing with 2.8 g of 4-fluoronitrobenzene it is heated for 2 hours to 100° C. bath temperature. After one more addition of 1.4 g of 4-fluoronitrobenzene it is heated for 45 minutes more to 100° C. After cooling, it was poured on ice and suctioned off. The filter cake is chromatographed over silica gel with acetone: hexane=1:1 as mobile solvent. 5.7 g (70% of theory) of 5-(4-nitrophenoxy)-4-methoxymethyl-beta-carboline-3-carboxylic acid ethyl ester with a melting point of 231°–232° C. is obtained.

Analogously there are produced:

5-(2-nitrophenoxy)-4-methyl-beta-carboline-3-carboxylic acid ethyl ester
melting point 241°–242° C.

5-(2-nitrophenoxy)-4-ethyl-beta-carboline-3-carboxylic acid ethyl ester 6-3(4-cyanophenoxy)-4-methoxymethyl-beta-carboline-3-carboxylic acid ethyl ester
melting point 226°–227° C.

6-(2-nitrophenoxy)-4-methoxymethyl-beta-carboline-3-carboxylic acid isopropyl ester
melting point 147°–150° C.

6-(2-formylphenoxy)-4-methoxymethyl-beta-carboline-3-carboxylic acid isopropyl ester
melting point 188°–192° C.

6-(2-cyanophenoxy)-4-methoxymethyl-beta-carboline-3-carboxylic acid isopropyl ester
melting point 170° C.

6-(2-cyano-3-chlorophenoxy)-4-methoxymethyl-beta-carboline-3-carboxylic acid isopropyl ester
melting point 117°–125° C.

6-(2-acetylphenoxy)-4-methoxymethyl-beta-carboline-3-carboxylic acid isopropyl ester
melting point 112°–117° C.

6-(2-cyano-4-fluorophenoxy)-4-methoxymethyl-beta-carboline-3-carboxylic acid isopropyl ester
melting point 228°–230° C.

6-(4-acetylphenoxy)-4-methoxymethyl-beta-carboline-3-carboxylic acid isopropyl ester
melting point 233° C.

5-(4-nitrophenoxy)-4-methyl-beta-carboline-3-carboxylic acid ethyl ester
melting point 225° C.

5-(4-nitrophenoxy)-4-ethyl-beta-carboline-3-carboxylic acid ethyl ester
melting point 217°–218° C.

5-(4-nitrophenoxy)-beta-carboline-3-carboxylic acid ethyl ester
melting point, greater than 242° C.

5-(4-nitro-2-chlorophenoxy)-4-methoxymethyl-beta-carboline-3-carboxylic acid ethyl ester 5-(4-nitro-3-methylphenoxy)-4-methoxymethyl-beta-carboline-3-carboxylic acid ethyl ester
melting point 212°–213° C.

5-(4-nitro-2-methylphenoxy)-4-methoxymethyl-beta-carboline-3-carboxylic acid ethyl ester
melting point 190°–192° C.

5-(4-ethoxycarbonylphenoxy)-4-methoxymethyl-beta-carboline-3-carboxylic acid ethyl ester
melting point 157° C.

6-(4-nitrophenoxy)-beta-carboline-3-carboxylic acid methyl ester 6-(4-nitrophenoxy)-beta-carboline-3-carboxylic acid ethyl ester
melting point, greater than 250° C.

6-(4-nitrophenoxy)-4-methyl-beta-carboline-3-carboxylic acid ethyl ester
melting point 288°–292° C.

6-(4-nitrophenoxy)-4-methoxymethyl-beta-carboline-3-carboxylic acid ethyl ester
melting point 231°–232° C.

6-(2-cyano-3-chlorophenoxy)-4-methyl-beta-carboline-3-carboxylic acid isopropyl ester
melting point 230°–232° C.

6-(2-cyano-6-fluorophenoxy)-4-methoxymethyl-beta-carboline-3-carboxylic acid isopropyl ester
melting point 175° C.

6-(2-cyano-3-fluorophenoxy)-4-methoxymethyl-beta-carboline-3-carboxylic acid isopropyl ester
melting point 208° C.

6-(2-isopropoxycarbonylphenoxy)-4-methoxymethyl-beta-carboline-3-carboxylic acid isopropyl ester
melting point 145° C.

6-(2-t-butoxycarbonylphenoxy)-4-methoxymethyl-beta-carboline-3-carboxylic acid isopropyl ester
melting point 136° C.

6-(4-fluoro-2-nitrophenoxy)-4-methoxymethyl-beta-carboline-3-carboxylic acid isopropyl ester 6-(4-nitro-3-chlorophenoxy)-4-methoxymethyl-beta-carboline-3-carboxylic acid isopropyl ester 6-(4-nitro-3-methylphenoxy)-4-methoxymethyl-beta-carboline-3-carboxylic acid isopropyl ester 6-(2-nitro-3-chlorophenoxy)-4-methoxymethyl-beta-carboline-3-carboxylic acid isopropyl ester 6-(2-nitro-3,5-dichlorophenoxy)-4-methoxymethyl-beta-carboline-3-carboxlyic acid isopropyl ester 6-(2-nitrophenoxy)-4-methoxymethyl-beta-carboline-3-carboxylic acid ethyl ester
melting point 153°–155° C.

6-(4-nitro-3-methoxyphenoxy)-4-methoxymethyl-beta-carboline-3-carboxylic acid ethyl ester
melting point 192°–203° C.

6-(4-nitro-2-methylphenoxy)-4-methoxymethyl-beta-carboline-3-carboxylic acid ethyl ester
melting point 184°–185° C.

6-(4-nitro-2-chlorophenoxy)-4-methoxymethyl-beta-carboline-3-carboxylic acid ethyl ester
melting point 195° C.

6-(4-nitro-3-methylphenoxy)-4-methoxymethyl-beta-carboline-3-carboxylic acid ethyl ester
melting point 183°–184° C.

6-(2-nitro-4-trifluoromethylphenoxy)-4-methoxymethyl-beta-carboline-3-carboxylic acid ethyl ester
melting point 90° C.

6-(4-ethoxycarbonylphenoxy)-4-methoxymethyl-beta-carboline-3-carboxylic acid ethyl ester
melting point 181° C.

6-(4-trifluoromethylphenoxy)-4-methoxymethyl-beta-carboline-3-carboxylic acid ethyl ester
melting point 226°–227° C.

6-(4-methylsulfonylphenoxy)-4-methoxymethyl-beta-carboline-3-carboxylic acid ethyl ester
melting point 204°–205° C.

5-(4-formylphenoxy)-4-methoxymethyl-beta-carboline-3-carboxylic acid ethyl ester
melting point 190°–192° C.

5-(2-nitro-4-chlorophenoxy)-4-methoxymethyl-beta-carboline-3-carboxylic acid ethyl ester
melting point 160°–162° C.

5(2-nitro-5-chlorophenoxy)-4-methoxymethyl-beta-carboline-3-carboxylic acid ethyl ester
melting point 155°–170° C.

6-(4-nitro-2-methylphenoxy)-4-methoxymethyl-beta-carboline-3-carboxylic acid isopropyl ester 6-(2-nitrophenoxy)-4-ethyl-beta-carboxylic acid ethyl ester 6-(2-nitro-4-methoxyphenoxy)-4-methoxymethyl-beta-carboline-3-carboxylic acid isopropyl ester 6-(4-nitro-3-methoxyphenoxy)-4-methoxymethyl-beta-carboline-3-carboxylic acid isopropyl ester 6-(4-nitro-3-cyanophenoxy)-4-methoxymethyl-beta-carboline-3-carboxylic acid isopropyl ester 6-(2-nitro-4-methylphenoxy)-4-methoxymethyl-beta-carboline-3-carboxylic acid isopropyl ester 6-(2-methoxy-4-nitrophenoxy)-4-methoxymethyl-beta-carboline-3-carboxylic acid isopropyl ester 6-(4-morpholinosulfamoylphenoxy)-4-methoxymethyl-beta-carboline-3-carboxylic acid ethyl ester
melting point 100° C. (decomp.)

6-(4-diethylsulfamoylphenoxy)-4-methoxymethyl-beta-carboline-3-carboxylic acid ethyl ester
melting point 179° C.

6-(2-ethylsulfonylphenoxy)-4-methoxymethyl-beta-carboline-3-carboxylic acid ethyl ester
melting point 196°–198° C.

EXAMPLE 4

5-(4-aminophenoxy)-4-methoxymethyl-beta-carboline-3-carboxylic acid ethyl ester 15 g of 5-(4-nitrophenoxy)-4-methoxymethyl-beta-carboline-3-carboxylic acid ethyl ester is hydrogenated in 450 ml of methanol: tetrahydrofuran=1:1 with 7.5 g of palladium on carbon (10%) at room temperature under hydrogen normal pressure. After filtering and concentrating, it is recrystallized from ethanol and 10.8 g (77% of theory) of 5-(4-aminophenoxy)-4-methoxymethyl-beta-carboline-3-carboxylic acid ethyl ester of a melting point of 222°–224° C. is obtained.

Analogously there are produced:

5-(4-aminophenoxy)-4-methyl-beta-carboline-3-carboxylic acid ethyl ester
melting point 170°–172° C.

5-(4-aminophenoxy)-4-ethyl-beta-carboline-3-carboxylic acid ethyl ester
melting point 235° C.

6-(4-aminophenoxy)-4-methyl-beta-carboline-3-carboxylic acid ethyl ester 6-(4-aminophenoxy)-4-methoxymethyl-beta-carboline-3-carboxylic acid ethyl ester
melting point 204°–234° C.

6-(4-amino-3-chlorophenoxy)-4-methoxymethyl-beta-carboline-3-carboxylic acid isopropyl ester 6-(4-amino-3-methylphenoxy)-4-methoxymethyl-beta-carboline-3-carboxylic acid isopropyl ester 6-(2-amino-3-chlorophenoxy)-4-methoxymethyl-beta-carboline-3-carboxylic acid isopropyl ester 6-(2-amino-3,5-dichlorophenoxy)-4-methoxymethyl-beta-carboline-3-carboxylic acid isopropyl ester 5-(2-amino-5-chlorophenoxy)-4-methoxymethyl-beta-carboline-3-carboxylic acid ethyl ester 6-(4-amino-2-methylphenoxy)-4-methoxymethyl-beta-carboline-3-carboxylic acid isopropyl ester 6-(4-fluoro-2-aminophenoxy)-4-methoxymethyl-beta-carboline-3-carboxylic acid isopropyl ester 6-(4-amino-2-chlorophenoxy)-4-methoxymethyl-beta-carboline-3-carboxylic acid isopropyl ester 6-(2-amino-4-methoxyphenoxy)-4-methoxymethyl-beta-carboline-3-carboxylic acid isopropyl ester 6-(4-amino-3-methoxyphenoxy)-4-methoxymethyl-beta-carboline-3-carboxylic acid isopropyl ester 6-(4-amino-3-cyanophenoxy)-4-methoxymethyl-beta-carboline-3-carboxylic acid isopropyl ester 6-(2-amino-4-methylphenoxy)-4-methoxymethyl-beta-carboline-3-carboxylic acid isopropyl ester 6-(2-methoxy-4-aminophenoxy)-4-methoxymethyl-beta-carboline-3-carboxylic acid isopropyl ester 5-(4-aminophenoxy)-4-methoxymethyl-beta-carboline-3-carboxylic acid isopropyl ester melting point, greater than 250° C.

Basically in an analogous way, however, with Raney nickel at catalyst and tetrahydrofuran as solvent, there are produced:

5-(4-amino-3-chlorophenoxy)-4-methoxymethyl-beta-carboline-3-carboxylic acid ethyl ester melting point 202°–204° C.

5-(4-amino-2-chlorophenoxy)-4-methoxymethyl-beta-carboline-3-carboxylic acid ethyl ester melting point 204° C.

6-(4-amino-2-chlorophenoxy)-4-methoxymethyl-beta-carboline-3-carboxylic acid ethyl ester melting point 95°–106° C.

EXAMPLE 5

5-Phenoxy-4-methoxymethyl-beta-carboline-3-carboxylic acid ethyl ester 978 mg of 5(-4-aminophenoxy)-4-methoxymethyl-beta-carboline-3-carboxylic acid ethyl ester is suspended in 2 ml of water and 10 ml of a 50% tetrafluoroboric acid. After cooling to 0° C., it is mixed drop by drop with a solution of 224 mg of sodium nitrite in 2 ml of water and stirred at 0° C. for ½ hour. Then it is mixed at the same temperature with a 60% hypophosphoric acid and 150 mg of copper(I) oxide, diluted with 10 ml of water and afterwards heated for ½ hour on the steam bath. After adjustment of the pH to 8 with soda and addition of ammonia, it is extracted with ethyl acetate. The ethyl acetate phase is evaporated and the residue chromatographed over silica gel with acetone: hexane=1:1 as eluant. 540 mg (57% of theory) of 5-phenoxy-4-methoxymethyl-beta-carboline-3-carboxylic acid ethyl ester with a melting point of 174°–176° C. is obtained.

Analogously there are produced:

5-phenoxy-beta-carboline-3-carboxylic acid ethyl ester melting point 246° C.

5-(3-chlorophenoxy)-4-methoxymethyl-beta-carboline-3-carboxylic acid ethyl ester melting point 194°–197° C.

5(-2-chlorophenoxy)-4-methoxymethyl-beta-carboline-3-carboxylic acid ethyl ester melting point 175°–177° C.

6-phenoxy-beta-carboline-3-carboxylic acid ethyl ester melting point 241°–242° C.

6-phenoxy-4-methyl-beta-carboline-3-carboxylic acid ethyl ester 6-phenoxy-4-methoxymethyl-beta-carboline-3-carboxylic acid ethyl ester melting point 172°–174° C.

6-(3-chlorophenoxy)-4-methoxymethyl-beta-carboline-3-carboxylic acid isopropyl ester melting point 164° C.

6-(3-methylphenoxy)-4-methoxymethyl-beta-carboline-3-carboxylic acid isopropyl ester melting point 170°–174° C.

6-(3,5-dichlorophenoxy)-4-methoxymethyl-beta-carboline-3-carboxylic acid isopropyl ester melting point 210° C.

6-(2-methylphenoxy)-4-methoxymethyl-beta-carboline-3-carboxylic acid isopropyl ester melting point 165°–170° C.

5-(2,5-dichlorophenoxy)-4-methoxymethyl-beta-carboline-3-carboxylic acid ethyl ester melting point 194°–196° C.

6-(4-methoxyphenoxy)-4-methoxymethyl-beta-carboline-3-carboxylic acid isopropyl ester 6-(3-cyanophenoxy)-4-methoxymethyl-beta-carboline-3-carboxylic acid isopropyl ester 6-(3-methoxyphenoxy)-4-methoxymethyl-beta-carboline-3-carboxylic acid isopropyl ester 6-(4-methylphenoxy)-4-methoxymethyl-beta-carboline-3-carboxylic acid isopropyl ester 6-(2-methoxyphenoxy)-4-methoxymethyl-beta-carboline-3-carboxylic acid isopropyl ester

EXAMPLE 6

5-(4-chlorophenoxy)-4-methoxymethyl-beta-carboline-3-carboxylic acid ethyl ester 195 mg 5-(4-aminophenoxy)-4-methoxymethyl-beta-carboline-3-carboxylic acid ethyl ester is suspended in a mixture of 2 ml of water and 2 ml of concentrated hydrochloric acid and, after cooling to 0° C., is mixed drop by drop with a solution of 35 mg of sodium nitrite in 0.5 ml of water. After the addition is completed, it is stirred for 45 minutes at 0° C., whereby a bright yellow solution results. To this is added at 0° C. drop by drop a solution which was previously prepared by addition of 69 mg of sodium sulfate in 0.5 ml of water to 250 mg of copper(II) sulfate, 5 H$_2$O and 87 mg of sodium chloride in 1 ml of water, suctioning off of the precipitate and dissolution in 0.5 ml of concentrated hydrochloric acid. After the addition is completed, a yellow precipitation has occurred and the mixture is then heated to the end of the development of gas on the steam bath. Then it is diluted with water, alkalized with ammonia solution and extracted with ethyl acetate. After evaporation of the organic phase, it is chromatographed over silica gel with methylene chloride: ethanol=10:1 as eluant. 130 mg (55% of theory) of 5-(-4-chlorophenoxy)-4-methoxymethyl-beta-carboline-3-carboxylic acid ethyl ester with a melting point of 207° C. is obtained.

Analogously there are produced:

5-(4-chlorophenoxy)-4-methyl-beta-carboline-3-carboxylic acid ethyl ester 5-(2,4-dichlorophenoxy)-4-methoxymethyl-beta-carboline-3-carboxylic acid ethyl ester melting point 156°–158° C.

6-(4-chlorophenoxy)-4-methoxymethyl-beta-carboline-3-carboxylic acid ethyl ester melting point 176°–188° C.

6-(4-chlorophenoxy)-4-methoxymethyl-beta-carboline-3-carboxylic acid ethyl ester melting point 178° C.

6-(2,4-dichlorophenoxy)-4-methoxymethyl-beta-carboline-3-carboxylic acid ethyl ester 5-(4-iodophenoxy)-4-methoxymethyl-beta-carboline-3-carboxylic acid ethyl ester melting point 200° C.

6-(2-bromophenoxy)-4-methoxymethyl-beta-carboline-3-carboxylic acid isopropyl ester melting point 152°–160° C.

6-(4-fluoro-2-chlorophenoxy)-4-methoxymethyl-beta-carboline-3-carboxylic acid isopropyl ester melting point 134°–144° C.

6-(2,3-dichlorophenoxy)-4-methoxymethyl-beta-carboline-3-carboxylic acid isopropyl ester
melting point 100°–101° C.
6-(4-piperidinoazophenoxy)-4-methoxymethyl-beta-carboline-3-carboxylic acid isopropyl ester
melting point 168°–174° C.
6-(4-bromophenoxy)-4-methoxymethyl-beta-carboline-3-carboxylic acid ethyl ester
melting point 169°–175° C.
6-(4-azidophenoxy)-4-methoxymethyl-beta-carboline-3-carboxylic acid ethyl ester
melting point 169°–175° C.

EXAMPLE 7

5-Phenoxy-4-methoxymethyl-beta-carboline-3-carboxylic acid isopropyl ester 540 mg of 5-phenoxy-4-methoxymethyl-beta-carboline-3-carboxylic acid ethyl ester in 30 ml of isopropanol is refluxed with 0.2 ml of titanium(IV) isopropylate for 2 hours. After concentration, it is mixed with 0.5N hydrochloric acid and extracted with ethyl acetate. The ethyl acetate phase is dried, filtered and concentrated and digested with diisopropyl ether. 450 mg (82% of theory) of 5-phenoxy-4-methoxymethyl-beta-carboline-3-carboxylic acid isopropyl ester with a melting point of 207°–209° C. is obtained.

Analogously there are produced:
5-phenoxy-4-methyl-beta-carboline-3-carboxylic acid isopropyl ester
5-(4-chlorophenoxy)-4-methyl-beta-carboline-3-carboxylic acid isopropyl ester
melting point 266°–268° C.
5-(4-chlorophenoxy)-4-methoxymethyl-beta-carboline-3-carboxylic acid isopropyl ester
melting point 216°–218° C.
5-(4-nitrophenoxy)-4-methyl-beta-carboline-3-carboxylic acid isopropyl ester
melting point 262° C.
5-(4-nitrophenoxy)-4-methoxymethyl-beta-carboline-3-carboxylic acid isopropyl ester
melting point 207°–209° C.
6-phenoxy-4-methoxymethyl-beta-carboline-3-carboxylic acid isopropyl ester
melting point 181° C.
6-(4-chlorophenoxy)-4-methoxymethyl-beta-carboline-3-carboxylic acid isopropyl ester
melting point 178°–181° C.
6-(4-cyanophenoxy)-4-methoxymethyl-beta-carboline-3-carboxylic acid isopropyl ester
melting point 226°–227° C.
6-(2-chlorophenoxy)-4-methoxymethyl-beta-carboline-3-carboxylic acid isopropyl ester
melting point 103°–109° C.
6-(4-isopropoxycarbonylphenoxy)-4-methoxymethyl-beta-carboline-3-carboxylic acid isopropyl ester
melting point 167° C.
6-(3-chloro-4-nitrophenoxy)-4-methoxymethyl-beta-carboline-3-carboxylic acid isopropyl ester
melting point 105°–115° C.
6-(2,4-dichlorophenoxy)-4-methoxymethyl-beta-carboline-3-carboxylic acid isopropyl ester
melting point 75°–78° C.
6-(4-flurophenoxy)-4-methoxymethyl-beta-carboline-3-carboxylic acid isopropyl ester
melting point 104°–116° C.
5(3-chlorophenoxy)-4-methoxymethyl-beta-carboline-3-carboxylic acid isopropyl ester
melting point 187°–189° C.
6-(3,4-dichlorophenoxy)-4-methoxymethyl-beta-carboline-3-carboxylic acid isopropyl ester
melting point 66°–68° C.

Example 8

5-Phenoxy-4-methoxymethyl-beta-carboline-3-carboxylic acid isopropyl ester 2 g of 5-(4-chlorophenoxy)-4-methoxymethyl-beta-carboline-3-carboxylic acid isopropyl ester in 40 ml of isopropanol is hydrogenated with 200 mg of palladium on carbon (10%) and 0.9 ml of triethylamine at room temperature under normal hydrogen pressure. After filtering off of the catalyst, concentration of the filtrate and digesting of the residue with diisopropyl ether, 1.4 g of 5-phenoxy-4-methoxymethyl-beta-carboline-3-carboxylic acid isopropyl ester with a melting point of 201°–203° C. is obtained.

Example 9

5-Phenoxy-4-methoxymethyl-beta-carboline-3-carboxylic acid t-butyl ester 300 mg of 5-phenoxy-4-methoxymethyl-beta-carboline-3-carboxylic acid is heated with 2 ml of aminal ester for 3 hours to 120° C., whereby a solution is produced. After diluting with water, it is extracted with ethyl acetate. The organic phase is dreid, filtered, concentrated and chromatographed over silica gel with acetone:hexane=1:1 as eluant. 130 mg of 5-phenoxy-4-methoxymethyl-beta-carboline-3-carboxylic acid t-butyl ester with a decomposition point of 150° C. is obtained.

Analogously there are produced:
5-(4-chlorophenoxy)-4-methoxymethyl-beta-carboline-3-carboxylic acid t-butyl ester
melting point 209°–210° C.
6-(3-chlorophenoxy)-4-methoxymethyl-beta-carboline-3-carboxylic acid t-butyl ester
melting point 159°–160° C.
6-(2-cyanophenoxy)-4-methoxymethyl-beta-carboline-3-carboxylic acid t-butyl ester
melting point 144° C.
6-(2-cyano-3-chlorophenoxy)-4-methoxymethyl-beta-carboline-3-carboxylic acid t-butyl ester
melting point 100° C.
6(-2,3-dichlorophenoxy)-4-methoxymethyl-beta-carboline-3-carboxylic acid t-butyl ester
melting point 203°–204° C.
6-(4-flurophenoxy)-4-methoxymethyl-beta-carboline-3-carboxylic acid t-butyl ester
melting point 189°–191° C.
5-(4-nitrophenoxy)-4-methoxymethyl-beta-carboline-3-carboxylic acid t-butyl ester
melting point 221°–222° C.
6-(4-chlorophenoxy)-4-methyl-beta-carboline-3-carboxylic acid t-butyl ester
6-phenoxy-4-methoxymethyl-beta-carboline-3-carboxylic acid t-butyl ester

Example 10

5-(4-chlorophenoxy)-4-methoxymethyl-beta-carboline-3-carboxylic acid isopropylamide 382 mg of 5-(4-chlorophenoxy)-4-methoxymethyl-beta-carboline-3-carboxylic acid in 10 ml of dimethylformamide is mixed with 380 mg of carbonyldiimidazole. After 2 hours stirring at room temperature, 1 ml of isopropylamine is added and stirred overnight. After mixing with water, it is extracted with ethyl acetate. The ethyl acetate phase is dried, filtered and concentrated. The residue is chromatographed over silica gel with methylene chloride: acetone=1:1 as eluant. 90 mg of 5-(4-chlorophenoxy)-4-methoxymethyl-beta-carboline-3-carboxylic acid isopropylamide with a melting point of 255° C. is obtained.

Analogously there are produced:
5-phenoxy-4-methoxymethyl-beta-carboline-3-carboxylic acid methylamide
  melting point 235° C.
5-(4-chlorophenoxy)-4-methoxymethyl-beta-carboline-3-carboxylic acid methylamide
  melting point 236° C. 5-(4-nitrophenoxy)-4-methoxymethyl-beta-carboline-3-carboxylic acid isopropylamide
6-phenoxy-4-methoxymethyl-beta-carboline-3-carboxylic acid isopropylamide
6-(4-chlorophenoxy)-4-methoxymethyl-beta-carboline-3-carboxylic acid isopropylamide
6-(2-chlorophenoxy)-4-methoxymethyl-beta-carboline-3-carboxylic acid isopropylamide
5-phenoxy-4-methoxymethyl-beta-carboline-3-carboxylic acid isopropylamide

Example 11

5-Phenoxy-4-methoxymethyl-beta-carboline-3-carboxylic acid 7.7 g of 5-phenoxy-4-methoxymethyl-beta-carboline-3-carboxylic acid ethyl ester is heated with 70 ml of 2N sodium hydroxide solution until a clear solution is produced (2 hours). Then, it is carefully acidified with 4N hydrochloric acid and afterwards stirred for 15 minutes at room temperature. After suctioning off and drying over $P_2O_5$ and KOH at 80° C., 7.2 g (100% of theory) of 5-phenoxy-4-methoxymethyl-beta-carboline-3-carboxylic acid is obtained.

Analogously there are produced:
5-(4-chlorophenoxy)-4-methoxymethyl-beta-carboline-3-carboxylic acid
5-(4-nitrophenoxy)-4-methoxymethyl-beta-carboline-3-carboxylic acid
6-(4-chlorophenoxy)-4-methyl-beta-carboline-3-carboxylic acid
6-phenoxy-4-methoxymethyl-beta-carboline-3-carboxylic acid
5-(4-nitrophenoxy)-4-methyl-beta-carboline-3-carboxylic acid
5-(4-nitrophenoxy)-beta-carboline-3-carboxylic acid
6-phenoxy-beta-carboline-3-carboxylic acid
6-phenoxy-4-methyl-beta-carboline-3-carboxylic acid
6-(4-nitrophenoxy)-beta-carboline-3-carboxylic acid
6-(4-nitrophenoxy)-4-methyl-beta-carboline-3-carboxylic acid
6-(4-chlorophenoxy)-4-methoxymethyl-beta-carboline-3-carboxylic acid
6-(4-bromophenoxy)-4-methoxymethyl-beta-carboline-3-carboxylic acid
6-(4-nitrophenoxy)-4-methoxymethyl-beta-carboline-3-carboxylic acid
6-(2-nitrophenoxy)-4-methoxymethyl-beta-carboline-3-carboxylic acid
6-(2-methyl-4-nitrophenoxy)-4-methoxymethyl-beta-carboline-3-carboxylic acid
6-(4-morpholinosulfamoylphenoxy)-4-methoxymethyl-beta-carboline-3-carboxylic acid
6-(4-methylsulfonylphenoxy)-4-methoxymethyl-beta-carboline-3-carboxylic acid
6-(-4-diethylsulfamoylphenoxy)-4-methoxymethyl-beta-carboline-3-carboxylic acid
6-(2-chlorophenoxy)-4-methoxymethyl-beta-carboline-3-carboxylic acid
6-(4-cyanophenoxy)-4-methoxymethyl-beta-carboline-3-carboxylic acid
6-(4-flurophenoxy)-beta-carboline-3-carboxylic acid
6-(2-chloro-4-nitrophenoxy)-4-methoxymethyl-beta-carboline-3-carboxylic acid
6-(2,4-dichlorophenoxy)-4-methoxymethyl-beta-carboline-3-carboxylic acid
6-(3-chlorophenoxy)-4-methoxymethyl-beta-carboline-3-carboxylic acid
6-(2-cyanophenoxy)-4-methoxymethyl-beta-carboline-3-carboxylic acid
6-(2-cyano-3-chlorophenoxy)-4-methoxymethyl-beta-carboline-3-carboxylic acid
6-(2,3-dichlorophenoxy)-4-methoxymethyl-beta-carboline-3-carboxylic acid
6-(4-fluorophenoxy)-4-methoxymethyl-beta-carboline-3-carboxylic acid.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A phenoxy-substituted beta-carboline of the formula

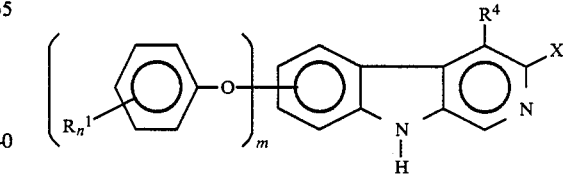

wherein
X is $COOR^3$, $CONHC_{1-3}$ alkyl or an oxadiazolyl radical of the formula

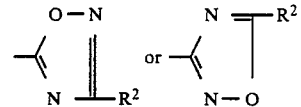

$R^2$ is H, $C_{1-6}$-alkyl or $C_{3-7}$ cycloalkyl,
$R^3$ is $C_{1-6}$-alkyl,
$R^4$ is hydrogen, $C_{1-6}$-alkyl or $C_{1-6}$-alkoxy-$C_{1-6}$-alkyl,
$R^1$ is halogen, $C_{1-6}$-alkyl, $C_{1-6}$-alkoxy, $C_{1-4}$-alkanoyl, phenyl, $C_{2-5}$ alkylenedioxy, trifluoromethyl, cyano, nitro, $C_{1-6}$-alkoxycarbonyl, azido, $SO_2R^6$, $SO_2NR^7R^8$, or $NR^9NR^{10}$,
$R^6$ is $C_{1-6}$-alkyl,
$R^7$ and $R^8$ independently are $C_{1-6}$-alkyl or together with the connecting nitrogen atom form a saturated hereto ring of 5 or 6 members, or such a ring wherein one or two $CH_2$ groups are replaced by O, S or N,
$R^9$ and $R^{10}$ independently are each hydrogen, $C_{1-6}$-alkyl, $C_{1-4}$-alkanoyl or together with the connecting nitrogen atom form a saturated hetero ring of 5 or 6 members, or such a ring wherein one or two CH$_2$ groups are replaced by O, S or N,
n is 0 to 5, and
m is 1–2,
with the proviso that X is not COOEt, when

 (a)

is 5-phenoxy and R$^4$ is methyl or when

 (b)

is 6-(4-methoxyphenoxy) and R$^4$ is methoxymethyl.

2. A compound of claim 1 wherein X is COOR$^3$.
3. A compound of claim 1 wherein R$^3$ is ethyl or isopropyl.
4. A compound of claim 1 wherein X is CONHalkyl.
5. A compound of claim 1 wherein X is oxadiazolyl.
6. A compouund of claim 1 wherein R$^4$ is methyl or methoxymethyl.
7. A compound of claim 1 wherein n is 1 or 2.
8. A compound of claim 1 wherein m is 1.
9. A compound of claim 1 wherein R$^1$ is chloro, nitro, amino, cyano, acetyl, morpholinylsulfamoyl, methylsulfonyl, or fluoro; or n is 0.
10. 5(-4-chlorophenoxy)-3-(3-ethyl-1,2,4-oxadiazol-5-yl)-4-methoxymethyl-beta carboline
   5-phenoxy-4-methyl-3-(3-ethyl-1,2,4-xoadiazol-5-yl)-beta-carboline
   5-(4-nitrophenoxy)-3-(3-ethyl-1,2,4-oxadiazol-5-yl)-beta-carboline
   5-(4-chlorophenoxy)-4-methyl-3-(3-ethyl-1,2,4-oxadiazol-5-yl)-beta-carboline
   6-phenoxy-4-methyl-3-(3-ethyl-1,2,4-oxadiazol-5-yl)-beta-carboline
   6-(4-chlorophenoxy)-4-methyl-3-(3-ethyl-1,2,4-oxadiazol-5-yl)-beta-carboline
   6-(4-aminophenoxy)-4-methyl-3-(3-ethyl-1,2,4-oxadiazol-5-yl)-beta-carboline
   6-(4-chlorophenoxy)-4-methoxymethyl-3-(3-ethyl-1,2,4-oxadiazol-5-yl)-beta-carboline
   6-(4-chlorophenoxy)-4-methoxymethyl-3-(3-cyclopropyl-1,2,4-oxadiazol-5-yl)-beta-carboline
   6-(4-morpholinosulfamoylphenoxy)-4-methoxymethyl-3-(3-cyclopropyl-1,2,4-oxadiazol-5-yl)-beta-carboline
   6-(4-4-methylsulfonylphenoxy)-4-methoxymethyl-3-(3-ethyl-1,2,4-oxadiazol-5-yl)-beta-carboline
   6-(2-chlorophenoxy)-4-methoxymethyl-3-(3-ethyl-1,2,4-oxadiazol-5-yl)-beta-carboline
   6-(2,4-dichlorophenoxy)-4-methoxymethyl-3-(3-ethyl-1,2,4-oxadiazol-5-yl)-beta-carboline
   5-(4-nitrophenoxy)-4-methoxymethyl-beta-carboline-3-carboxylic acid ethyl ester
   5-(4-nitro-2-chlorophenoxy)-4-methoxymethyl-beta-carboline-3-carboxylic acid ethyl ester
   6-(4-nitrophenoxy)-4-methyl-beta-carboline-3-carboxylic acid ethyl ester
   6-(4-nitrophenoxy)-4-methoxymethyl-beta-carboline-3-carboxylic acid ethyl ester
   5-(4-aminophenoxy)-4-methoxymethyl-beta-carboline-3-carboxylic acid ethyl ester
   5-phenoxy-4-methoxymethyl-beta-carboline-3-carboxylic acid ethyl ester
   5-(3-chlorophenoxy)-4-methoxymethyl-beta-carboline-3-carboxylic acid ethyl ester
   5-(2-chlorophenoxy)-4-methoxymethyl-beta-carboline-3-carboxylic acid ethyl ester
   6-phenoxy-4-methoxymethyl-beta-carboline-3-carboxylic acid ethyl ester
   5-(4-chlorophenoxy)-4-methoxymethyl-beta-carboline-3-carboxylic acid ethyl ester
   5-(4-chlorophenoxy)-4-methyl-beta-carboline-3-carboxylic acid ethyl ester
   5-(2,4-dichlorophenoxy)-4-methoxymethyl-beta-carboline-3-carboxylic acid ethyl ester
   6-(4-chlorophenoxy)-4-methoxymethyl-beta-carboline-3-carboxylic acid ethyl ester
   5-(2-chlorophenoxy)-4-methoxymethyl-3-(3-ethyl-1,2,4-oxadiazol-5-yl)-beta-carboline
   5-(3-chlorophenoxy)-4-methoxymethyl-3-(3-ethyl-1,2,4-oxadiazol-5-yl)-beta-carboline
   5-(2-chlorophenoxy)-4-methoxymethyl-beta-carboline-3-carboxylic acid isopropyl ester
   6-(2-nitrophenoxy)-4-methoxymethyl-beta-carboline-3-carboxylic acid isopropyl ester
   6-(2-cyano-3-chlorophenoxy)-4-methoxymethyl-beta-carboline-3-carboxylic acid isopropyl ester
   6-(2-cyanophenoxy)-4-methoxymethyl-beta-carboline-3-carboxylic acid isopropyl ester
   6-(4-acetylphenoxy)-4-methoxymethyl-3-(3-ethyl-1,2,4-oxadiazol-5-yl)-beta-carboline
   6-(3-methylphenoxy)-4-methoxymethyl-beta-carboline-3-carboxylic acid isopropyl ester
   6-(3-chlorophenoxy)-4-methoxymethyl-beta-carboline-3-carboxylic acid isopropyl ester
   6-(2,4-dichlorophenoxy)-4-methoxymethyl-beta-carboline-3-carboxylic acid ethyl ester
   5-phenoxy-4-methoxymethyl-beta-carboline-3-carboxylic acid isopropyl ester
   5-(4-chlorophenoxy)-4-methyl-beta-carboline-3-carboxylic acid isopropyl ester
   5-(4-chlorophenoxy)-4-methoxymethyl-beta-carboline-3-carboxylic acid isopropyl ester
   6-(4-chlorophenoxy)-4-methoxymethyl-beta-carboline-3-carboxylic acid isopropyl ester
   6-(4-fluorophenoxy)-4-methoxymethyl-beta-carboline-3-carboxylic acid isopropyl ester
   6-(3,4-dichlorophenoxy)-4-methoxymethyl-beta-carboline-3-carboxylic acid isopropyl ester
   5-phenoxy-4-methoxymethyl-beta-carboline-3-carboxylic acid t-butyl ester
   6-phenoxy-4-methoxymethyl-beta-carboline-3-carboxylic acid t-butyl ester or
   5-(4-chlorophenoxy)-4-methoxymethyl-beta-carboline-3-carboxylic acid isopropylamide.
11. A pharmaceutical composition comprising a compound of claim 1 and a pharmaceutically acceptable carrier.
12. A pharmaceutical composition comprising 0.05 to 100 mg. of a compound of claim 1 and a pharmaceutically acceptable carrier.
13. A method of achieving an anxiolytic effect comprising administering a compound of claim 1.
14. A method of achieving an anticonvulsant effect comprising administering a compound of claim 1.
15. A method of binding a benzodiazepine receptor comprising administering a compound of claim 1.

16. A compound of claim 1 wherein n is 1-5.

17. A method of enhancing memory comprising administering a compound of claim 1.

18. A method of achieving an amnestic effect comprising administering a compound of claim 1.

19. 5-(4-chlorophenoxy)-4-methoxymethyl-beta-carboline-3-carboxylic acid isopropyl ester, a compound of claim 1.

20. A method of enhancing memory comprising administering a compound of claim 19.

21. A method of achieving an amnestic effect comprising administering a compound of claim 19.

22. A compound of claim 1, wherein $R^1$ is halogen, $C_{1-6}$-alkyl, $C_{1-4}$-alkanoyl, phenyl, $C_{2-5}$-alkylenedioxy, trifluoromethyl, cyano, nitro, $C_{1-6}$-alkoxy carbonyl, azido, $SO_2R^6$, $SO_2NR^7R^8$ or $NR^9NR^{10}$.

* * * * *